(12) United States Patent
Ko et al.

(10) Patent No.: US 11,365,452 B2
(45) Date of Patent: Jun. 21, 2022

(54) COMPOSITION FOR DIAGNOSING OR PREDICTING RISK OF METABOLIC SYNDROME OR METABOLIC SYNDROME-RELATED DISEASES USING HUMAN ORAL MICROBIOME

(71) Applicants: KoBioLabs, Inc., Seoul (KR); Seoul National University R&DB Foundation, Seoul (KR)

(72) Inventors: GwangPyo Ko, Seoul (KR); Jiyeon Si, Ansan-si (KR); Cheonghoon Lee, Paju-si (KR)

(73) Assignees: KOBIOLABS, INC., Seoul (KR); SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 118 days.

(21) Appl. No.: 16/316,662

(22) PCT Filed: Jul. 20, 2017

(86) PCT No.: PCT/KR2017/007841
§ 371 (c)(1),
(2) Date: Jan. 10, 2019

(87) PCT Pub. No.: WO2018/021761
PCT Pub. Date: Feb. 1, 2018

(65) Prior Publication Data
US 2019/0264262 A1 Aug. 29, 2019

(30) Foreign Application Priority Data
Jul. 25, 2016 (KR) .................. 10-2016-0094299

(51) Int. Cl.
| | | |
|---|---|---|
| C12Q 1/68 | (2018.01) | |
| C12Q 1/689 | (2018.01) | |
| C12Q 1/02 | (2006.01) | |
| G01N 33/569 | (2006.01) | |

(52) U.S. Cl.
CPC ............. *C12Q 1/689* (2013.01); *C12Q 1/025* (2013.01); *C12Q 1/68* (2013.01); *G01N 33/569* (2013.01); *C12Q 2600/112* (2013.01); *C12Q 2600/118* (2013.01); *C12Q 2600/136* (2013.01); *C12Q 2600/16* (2013.01)

(58) Field of Classification Search
CPC .................... C12Q 1/689; C12Q 2600/112
See application file for complete search history.

(56) References Cited

U.S. PATENT DOCUMENTS

| | | | |
|---|---|---|---|
| 2012/0196764 A1* | 8/2012 | Zhang .............. | G01N 33/57438 506/9 |
| 2013/0065769 A1 | 3/2013 | Wong | |
| 2014/0093478 A1 | 4/2014 | Turnbaugh et al. | |
| 2014/0328803 A1* | 11/2014 | McKenzie ............. | A61K 35/37 424/93.3 |
| 2016/0030494 A1 | 2/2016 | Henn et al. | |

FOREIGN PATENT DOCUMENTS

| | | |
|---|---|---|
| EP | 2927327 | 10/2015 |
| KR | 10-1445243 | 9/2014 |
| WO | 2014-179959 | 11/2014 |

OTHER PUBLICATIONS

Chen et al. (2015) "Oral microbiota and risk for esophageal squamous cell carcinoma in a high-risk area of China" PLoS ONE 10(12):1-16 (Year: 2015).*
Orlando et al. (1998) "Developments in quantitative PCR" Clin Chem Lab Med 36(5): 255-269. (Year: 1998).*
Goodson et al. (2009) "Is obesity an oral bacterial disease?" J Dent Res 88(6): 519-523. (Year: 2009).*
Kumar et al., "Pyrosequencing reveals unique microbial signatures associated with healthy and failing dental implants", (2012) J Clin Periodontol. 39(5):1-15 (Year: 2012).*
Daubert et al., "Prevalence and predictive factors for peri-implant disease and implant failure: A cross-sectional analysis", (2015) J Periodontol 86(3):pp. 1 (Year: 2015).*
Golden State Dentistry, "Deep Cleaning: Is it necessary?", (2015): pp. 1-2. (Year: 2015).*
Rekha et al., Designing and validation of genus-specific primers for human gut flora study, (2006) E J Biotech: 9(5): 505-511 (Year: 2006).*
Rani et al., Changes in bacterial profile during amebiasis: demonstration of anaerobic bacteria in ALA pus samples (2006), Am. J. Trop. Med. Hyg. 75(5)): 880-885 (Year: 2006).*
Medical University of Vienna, "The oral and gut microbiomes are perturbed in rheumatoid arthritis and partly normalized after treatment", Irina Gessl JC Translational Immunology, Nature medicine Aug. 2015.
Emmanouil Angelakis et al., "Samples and techniques highlighting the links between obesity and microbiota", Microbial Pathogenesis, Jan. 2016, pp. 1-8.

(Continued)

*Primary Examiner* — Jehanne S Sitton
(74) *Attorney, Agent, or Firm* — Lex IP Meister, PLLC (57) ABSTRACT

The present invention relates to markers being capable of predicting or diagnosing the risk of metabolic syndrome or metabolic syndrome-related diseases and their use. More particularly, the present invention relates to a composition, a kit and a method for predicting or diagnosing the risk of metabolic syndrome or metabolic syndrome-related diseases by detecting *Neisseria* spp., *Granulicatella* spp., and/or *Peptococcus* spp. in a test sample.

6 Claims, 9 Drawing Sheets
(8 of 9 Drawing Sheet(s) Filed in Color)

Specification includes a Sequence Listing.

(56) References Cited

OTHER PUBLICATIONS

J. Sung et al., "Healthy Twin: A Twin-Family Study of Korea—Protocols and Current Status", Twin Research and Human Genetics, 2006, vol. 9, No. 6, p. 844-848.
J.G. Caporaso et al., "Ultra-high-throughput microbial community analysis on the Illumina HiSeq and MiSeq platforms", The ISME Journal, 2012, vol. 6, pp. 1621-1624.
J.G. Caporaso et al., "QIIME allows analysis of high-throughput community sequencing data", Nature Methods, 2010, vol. 7, No. 5, p. 335-336.
M.G. Langille et al., "Predictive functional profiling of microbial communities using 16S rRNA marker gene sequences", Nature Biotechnology, 2013, vol. 31, No. 9, p. 814-821.
N. Segata et al., "Metagenomic biomarker discovery and explanation", Genome Biology, 2011, vol. 12, No. 6, R60.
J. He et al, "The oral microbiome diversity and its relation to human diseases", Folia Microbiol, 2015, vol. 60, pp. 69-80.
P. Jorth et al., "Metatranscriptomics of the human oral microbiome during health and disease", MBio, 2014, vol. 5, issue 2, thesis No. e01012-14, internal pp. 1-10.
J. Farrell et al., "Variations of oral microbiota are associated with pancreatic diseases including pancreatic cancer", GUT, 2012, vol. 61, No. 4, p. 582-588.
DTW Wong, "Salivary Diagnostics", Operative Dentistry, 2012, 37-6, pp. 562-570.
R. Rekha et al., "Designing and validation of genus-specific primers for human gut flora study", Electronic Journal of Biotechnology, 2005, vol. 9, No. 5.
Fak Frida et al., "Oral microbiota in patients with atherosclerosis", Atherosclerosis, Elsevier, Amsterdam, NL, vol. 243, No. 2. pp. 573-578, XP029320280, Oct. 24, 2015.
J.M. Goodson et al., "Is Obesity an Oral Bacterial Disease?", Journal of Dental Research, vol. 88, No. 6, pp. 519-523, XP055026788, Jun. 1, 2009.
Cecilia C. Zeigler et al., "Microbiota in the Oral Subgingival Biofilm Is Associated With Obesity in Adolescence", Obesity Research, vol. 20, No. 1, pp. 157-164, XPQ55665980, Jan. 1, 2012.
R. C. V. Casarin et al., "Subgingival biodiversity in subjects with uncontrolled type-2 diabetes and chronic periodontitis", Journal of Periodontal Research, vol. 48, No. 1, pp. 30-36, XP055665957, Feb. 1, 2013.
Jiyeon Si et al., "Oral Microbiota: Microbial Biomarkers of Metabolic Syndrome Independent of Host Genetic Factors", Frontiers in Cellular and Infection Microbiology, vol. 7, XP055666031, Dec. 15, 2017.
EPO, European Search Report of the corresponding European Patent Application No. 17834703.5., dated Feb. 14, 2020.

* cited by examiner

SEQUENCE LISTING

<160> NUMBER OF SEQ ID NOS: 16

<210> SEQ ID NO 1
<211> LENGTH: 24
<212> TYPE: DNA
<213> ORGANISM: Artificial Sequence

```
<220> FEATURE:
<223> OTHER INFORMATION: forward primer for amplification of peptococcus
      16S rRNA

<400> SEQUENCE: 1
ggtgccgcag taaacacaat aagt                                            24

<210> SEQ ID NO 2
<211> LENGTH: 20
<212> TYPE: DNA
<213> ORGANISM: Artificial Sequence
<220> FEATURE:
<223> OTHER INFORMATION: reverse primer for amplification of peptococcus
      16S rRNA

<400> SEQUENCE: 2
aaggcccggg aacgtattca                                                 20

<210> SEQ ID NO 3
<211> LENGTH: 22
<212> TYPE: DNA
<213> ORGANISM: Artificial Sequence
<220> FEATURE:
<223> OTHER INFORMATION: forward primer for amplification of
      Granulicatella 16S rRNA

<400> SEQUENCE: 3
caagcttctg ctgatggatg ga                                              22

<210> SEQ ID NO 4
<211> LENGTH: 21
<212> TYPE: DNA
<213> ORGANISM: Artificial Sequence
<220> FEATURE:
<223> OTHER INFORMATION: reverse primer for amplification of
      Granulicatella 16S rRNA

<400> SEQUENCE: 4
ctcaggtcgg ctatgcatca c                                               21

<210> SEQ ID NO 5
<211> LENGTH: 20
<212> TYPE: DNA
<213> ORGANISM: Artificial Sequence
<220> FEATURE:
<223> OTHER INFORMATION: forward primer for amplification of Neisseria
      elongata 16s rRNA

<400> SEQUENCE: 5
catgccgcgt gtctgaagaa                                                 20

<210> SEQ ID NO 6
<211> LENGTH: 21
<212> TYPE: DNA
<213> ORGANISM: Artificial Sequence
<220> FEATURE:
<223> OTHER INFORMATION: reverse primer for amplification of Neisseria
      elongata 16s rRNA

<400> SEQUENCE: 6
ccgtcagcag aaacgggtat t                                               21

<210> SEQ ID NO 7
<211> LENGTH: 60
<212> TYPE: DNA
<213> ORGANISM: Artificial Sequence
<220> FEATURE:
```

<223> OTHER INFORMATION: Forward primer prepared by using conserved
      bacterial primer 515F

<400> SEQUENCE: 7
aatgatacgg cgaccaccga gatctacact atggtaattg tgtgccagcm gccgcggtaa    60

<210> SEQ ID NO 8
<211> LENGTH: 56
<212> TYPE: DNA
<213> ORGANISM: Artificial Sequence
<220> FEATURE:
<223> OTHER INFORMATION: Reverse primer prepared by using conserved
      bacterial primer 806R

<400> SEQUENCE: 8
caagcagaag acggcatacg agatagtcag tcagccggac tachvgggtw tctaat    56

<210> SEQ ID NO 9
<211> LENGTH: 29
<212> TYPE: DNA
<213> ORGANISM: Artificial Sequence
<220> FEATURE:
<223> OTHER INFORMATION: adapter sequences of SEQ ID NO 7

<400> SEQUENCE: 9
aatgatacgg cgaccaccga gatctacac    29

<210> SEQ ID NO 10
<211> LENGTH: 10
<212> TYPE: DNA
<213> ORGANISM: Artificial Sequence
<220> FEATURE:
<223> OTHER INFORMATION: pad sequences of SEQ ID NO 7

<400> SEQUENCE: 10
tatggtaatt    10

<210> SEQ ID NO 11
<211> LENGTH: 2
<212> TYPE: DNA
<213> ORGANISM: Artificial Sequence
<220> FEATURE:
<223> OTHER INFORMATION: linker sequences of SEQ ID NO 7

<400> SEQUENCE: 11 gt    2

<210> SEQ ID NO 12
<211> LENGTH: 19
<212> TYPE: DNA
<213> ORGANISM: Artificial Sequence
<220> FEATURE:
<223> OTHER INFORMATION: conservative bacterial primers 515F

<400> SEQUENCE: 12
gtgccagcmg ccgcggtaa    19

<210> SEQ ID NO 13
<211> LENGTH: 24
<212> TYPE: DNA
<213> ORGANISM: Artificial Sequence
<220> FEATURE:
<223> OTHER INFORMATION: adapter sequences of SEQ ID NO 8

<400> SEQUENCE: 13
caagcagaag acggcatacg agat    24

```
<210> SEQ ID NO 14
<211> LENGTH: 10
<212> TYPE: DNA
<213> ORGANISM: Artificial Sequence
<220> FEATURE:
<223> OTHER INFORMATION: 12-barcode sequences of SEQ ID NO 8

<400> SEQUENCE: 14
agtcagtcag                                                          10

<210> SEQ ID NO 15
<211> LENGTH: 2
<212> TYPE: DNA
<213> ORGANISM: Artificial Sequence
<220> FEATURE:
<223> OTHER INFORMATION: linker sequences of SEQ ID NO 8

<400> SEQUENCE: 15 cc                                                                   2

<210> SEQ ID NO 16
<211> LENGTH: 20
<212> TYPE: DNA
<213> ORGANISM: Artificial Sequence
<220> FEATURE:
<223> OTHER INFORMATION: preserved bacterial primer 806R

<400> SEQUENCE: 16
ggactachvg ggtwtctaat                                               20
```

COMPOSITION FOR DIAGNOSING OR PREDICTING RISK OF METABOLIC SYNDROME OR METABOLIC SYNDROME-RELATED DISEASES USING HUMAN ORAL MICROBIOME

TECHNICAL FIELD

The present invention relates to a biomarker for predicting or diagnosing the risk of metabolic syndrome or metabolic syndrome-related diseases by using an oral microbiome and a method of non-invasively predicting or diagnosing the risk of metabolic syndrome or metabolic syndrome related disease.

RELATED ART

Obesity means the accumulation of unnecessarily excessive fat, and has various complications including cardiovascular disease, diabetes, arthritis and hyperlipemia. The complications are caused by the combination of genetic factors and environmental factor caused by western diet changes and deficient exercise. All elements of the metabolic syndrome are associated with insulin resistance, and thus insulin resistance has been identified as the most convincing cause of metabolic syndrome with obesity.

Metabolic syndrome is the most common risk factor for these diseases and is caused by various risk factors of the diseases at the same time. For example, the criteria used to define the metabolic syndrome vary from an organization to organization in the numerical value and contents, and thus, the prevalence and the risk are different on the used criteria. For example, the World Health Organization (WHO) and the European Insulin Resistance Research Group (EGIR) define the criteria focusing primarily on insulin resistance, but the National Cholesterol Education Program (NCEP ATP III) focus on abdominal obesity, which is practical criteria but does not reflect insulin resistance well. The criteria used for diagnosing the metabolic syndrome are based on unclear baseline values, and thus causes the problems from defining the patients with metabolic syndrome to establishing metabolic syndrome-specific treatment methods. Therefore, there is a need for a new diagnostic method that develops incomplete diagnostic criteria used conventionally and that encompasses all the criteria.

All microbial species including non-culturing microorganisms can be identified according to the analysis method of microorganisms using the next generation sequencing. The method is to identify microbial species using 16s rRNA genes which are conserved in all bacteria, and the hypervariable region, and to identify the relationship between microbial genome diversity and the disease. These microbial analysis methods have removed the conventional cultivation possibility used for the research on the relationship between existing bacteria and diseases, and have made a great improvement in that they have been reevaluated from the whole point of view. In particular, they have proved the epidemic relationship between intestinal microorganisms and obesity.

DISCLOSURE

Technical Problem

The present invention relates to a composition for predicting or diagnosing risk of a metabolic syndrome or metabolic syndrome-related diseases by using a non-invasive method, comprising one or more microorganisms selected from the group consisting of *Neisseria* spp., *Granulicatella* spp., and *Peptococcus* spp., or a kit for predicting or diagnosing risk of metabolic syndrome or metabolic syndrome-related diseases comprising the same.

Another object of the present invention is to provide a method of detecting or a kit of detecting one or more microorganisms selected from the group consisting of *Neisseria* spp., *Granulicatella* spp., and *Peptococcus* spp., from a sample of subject, in order to provide information required for predicting or diagnosing risk of a metabolic disease or metabolic disease-related disease.

It is still another object of the present invention to provide a method of screening a therapeutic agent for treating metabolic disease or metabolic disease-related disease, comprising a step of detecting change in one or more microbiota selected from the group consisting of *Neisseria* spp., *Granulicatella* spp., and *Peptococcus* spp., after treating with a candidate material.

Technical Solution

In order to achieve the object, the inventors of the present invention have developed a technique for early diagnosis of the occurrence and risk of metabolic syndrome based on the identification of the relationship between microorganisms and clinical markers of metabolic syndromes in healthy Korean twins.

An embodiment of the present invention is to provide a composition for predicting or diagnosing metabolic syndrome or metabolic syndrome-related diseases, comprising a detecting agent for detecting one or more microorganisms selected from the group consisting of *Neisseria* spp., and *Granulicatella* spp., and *Peptococcus* spp.

The present invention specifically identifies a specific increase of the population of *Neisseria* spp., and *Granulicatella* spp., and a specific decease of *Peptococcus* spp. in an oral cavity of patient with metabolic syndrome, and thus, provides one or more microbiota selected from the group consisting of *Neisseria* spp., *Granulicatella* spp., and *Peptococcus* spp., as biomarkers for predicting or diagnosing the occurrence and the risk of metabolic syndrome or metabolic syndrome-related diseases, on the basis of the identification.

In a specific example of the present invention, the twins were studied to investigate the relationship between oral microbiota and metabolic disease or related diseases, excluding the influence of human genetic and physiological factors on oral microbiota. As a result, it was confirmed that *Neisseria* spp., and *Granulicatella* spp. were specifically detected at a high level in a metabolic syndrome patient group, and *Peptococcus* spp. was detected specifically at a low level (Examples 5 and 6).

*Neisseria* spp. is a Gram-negative bacterium in the mucosa, and includes for example, *N. elongata*, *N. meningitides*, and *N. gonorrhoeae*, preferably, *N. elongata*. *Granulicatella* spp. has been initially classified as nutritionally variant *streptococcus* (NVS) and has been reported to grow in the respiratory, gastrointestinal, and reproductive tracts and clinically associated with endocarditis. For example, *Granulicatella* spp. of the present invention may contain *G. adiacens* which has a stronger infectious ability than other strains of bacteria due to the strong adhesion known as one factor.

*Peptococcus* spp. is a Gram-positive coccoid bacterium, which is characterized in that it is introduced into mucous membranes such as oral cavity, colon, respiratory tract and the like.

*Neisseria* spp., and *Granulicatella* spp., and *Peptococcus* spp. are microorganisms in oral cavity, and thus, the composition for predicting or diagnosing risk of a metabolic syndrome or metabolic syndrome-related diseases in the present invention is characterized in the application to a sample collected from the oral cavity.

As used herein, the term "marker used for diagnosis" or "diagnostic marker" refers to a substance that is a criterion for distinguishing metabolic syndrome from non-metabolic syndrome, and includes various organic biomolecules showing an increase or a decrease in a sample of metabolic syndrome or metabolic syndrome-related diseases. For the purpose of the present invention, the diagnostic marker of the present invention can be used to refer to *Neisseria* spp., and *Granulicatella* spp., and/or *Peptococcus* spp. or their microbiota showing specifically high or low levels of expression in a sample of a patient having a metabolic syndrome or a metabolic syndrome related disease.

Conventional methods for predicting or diagnosing the risk of metabolic syndrome differ in the numerical value and content of each diagnostic organization, and do not reflect the overall characteristics of the metabolic syndrome also in predicting or diagnosing the risk by using specific symptoms such as insulin resistance and abdominal obesity as an index, and syndrome, resulting in the inaccurate diagnostic criteria. However, the present invention has an advantage in the prediction or diagnosis of metabolic syndrome, without being limited to specific symptoms.

Preferably, the detectable agent is a substance which can be used to detect the presence of *Neisseria* spp., and *Granulicatella* spp., and/or *Peptococcus* spp. For example, the detectable agent can be at least one selected from the group consisting of primers, probes, antisense oligonucleotides, platamers and antibodies for detecting the organic biomolecules such as proteins, nucleic acids, lipids, glycolipids, glycoproteins and saccharides (monosaccharides, disaccharides, oligosaccharides, etc.) which are specifically present in *Neisseria* spp., and *Granulicatella* spp., and/or *Peptococcus* spp.

In the present invention, the detectable agent of microorganism may be an antibody, and the microorganism may be detected using an immunological method based on an antigen-antibody reaction. The analysis methods include Western blotting, enzyme linked immunosorbent as (ELISA), radioimmunoassay (RIA), radioimmunodiffusion, Ouchterlony immunodiffusion, rocket immunoassay Immunoprecipitation assays, complement fixation assays, fluorescence activated cell sorters (FACS), protein chips, and the like, but not limited thereto.

Preferably, the agent capable of detecting the microorganism is a microorganism-specific primer. The term, "primer" refers to a primer capable of forming a base pair complementary to a template strand, and to a nucleotide sequence of 7 to 50 bases functioning as a starting point for replicating the template. The primers are usually synthesized, but may be used as naturally occurring nucleotide sequence. The sequence of the primer does not necessarily have to be exactly the same as the sequence of the template, but is sufficiently complementary so long as it can hybridize with the template. Additional features that do not alter the basic properties of the primer can be incorporated to the primers. Examples of the additional features include, but are not limited to, methylation, capping, substitution of one or more nucleotides with its derivatives, and the nucleotide modification.

Preferably, the primers used in the present invention are selected from the group consisting of *Neisseria* spp. (Farrell, J., et al., Variants of oral microbiota associated with pancreatic diseases including pancreatic cancer. GUT, 2012. 61, p. 582-588), *Granulicatella* spp. (Farrell, J., et al., Variations of oral microbiota are associated with pancreatic diseases including pancreatic cancer. GUT, 2012.61: p. 582-588) and *Peptococcus* spp. (Rekha, R., et al., Designing and validation of genus-specific primers for human gut flora study. Electron J Biotechnol, 2005.9(5): p. 0-0). Preferably, the primer may be the primer shown in Table 1.

TABLE 1

| Bacterium | Classification | Nucleotide sequence | SEQ ID NO |
|---|---|---|---|
| *Peptococcus* spp. | Forward | 5'-GGTGCCGCAGTAAACACAATAAGT-3' | 1 |
| | Reverse | 5'-AAGGCCCGGGAACGTATTCA-3' | 2 |
| *Granulicatella adiacens* | Forward | 5'-CAAGCTTCTGCTGATGGATGGA-3' | 3 |
| | Reverse | 5'-CTCAGGTCGGCTATGCATCAC-3' | 4 |
| *Neisseria elongata* | Forward | 5'- CATGCCGCGTGTCTGAAGAA-3' | 5 |
| | Reverse | 5'- CCGTCAGCAGAAACGGGTATT-3' | 6 |

The 16s rRNA is a 30S subunit of the prokaryotic ribosome. Most of the 16s rRNA is conserved in the rRNA, while some regions exhibit high sequence diversity. In particular, there is little diversity among same species, but large diversity among different species, so that the sequence of 16S rRNA can be compared to identify prokaryotes effectively.

The metabolic syndrome related diseases may be at least one selected from the group consisting of obesity, hypertension, diabetes, insulin resistance syndrome, hyperlipidemia, hypercholesterolemia, cancer, cardiovascular disease, inflammatory bowel disease, atopy, and allergic diseases. Preferably, the metabolic syndrome related disorder may be hypertension.

For example, the obesity such as abdominal obesity in which the waist circumference is 90 cm or more for a male and 85 cm or more for a female, the hypertension in which a blood pressure is 130/85 mmHg, the diabetes in which a fasting blood glucose is 100 mg/dL or higher. In addition, when the blood triglyceride level is 150 mg/dL or more, the hypercholesterolemia means the condition that the HDL cholesterol level in the blood is 40 mg/dL or lower for male and 50 mg/dL or lower for female. The metabolic syndrome may be at least one selected from the group consisting of obesity, hypertension, hyperglycemia, hyperlipidemia such as hypertriglyceridemia and low HDL cholesterol, preferably three, or more preferably five states having the symptoms. The metabolic disorder or metabolic disease refers to a disease caused by metabolic abnormalities of glucose, fat, protein and the like.

For example, the composition of the present invention can be used for predicting or diagnosing the risk of metabolic syndrome satisfying one or more, or preferably three or more criteria selected from the group consisting of 1) to 5).

1) Waist circumference: 90 cm or higher for male and 85 cm or higher for female,
2) Blood triglyceride level: 150 mg/dL or more,
3) Serum HDL cholesterol level: less than 40 mg/dL for male and less than 50 mg/dL for female,
4) Blood pressure: 130/85 mmHg or more; and
5) Fasting blood glucose: 100 mg/dL or more.

For example, the selection criteria can be used to predict or diagnose the risk of metabolic disease or metabolic disease-related, in case of an Asian subject.

The risk prediction is to determine whether the subject is likely to develop metabolic syndrome or metabolic syndrome-related diseases and to identify the risk of metabolic syndrome or metabolic syndrome-related diseases. They can be used clinically to make treatment decisions by delaying the onset of the disease or preventing it from developing, or by selecting the most appropriate treatment method. In addition, the term "diagnosis" means the confirmation of the presence or characteristic of a pathological condition. For the purpose of the present invention, the diagnosis may mean the confirmation on whether or not a metabolic disease has occurred.

As another example of the present invention, the composition comprising a microorganism detecting agent of the present invention may be provided in the form of a kit for predicting or diagnosing the risk of metabolic syndrome or metabolic syndrome-related diseases. The kit of the present invention not only includes a detection agent for detecting the microorganisms, such as primers, probes, antisense oligonucleotides, aptamers and/or antibodies, as well as one or more other components, solutions, or devices which can be used suitable for the analyzing method.

The description for the composition of prediction or diagnosis of risk of metabolic syndrome or metabolic syndrome-related diseases may be applied to a kit for prediction or diagnosis risk of metabolic syndrome or metabolic syndrome-related diseases.

As a specific example, a kit containing a primer specific to the microorganism in the present invention may be a kit containing essential elements for carrying out an amplification reaction such as PCR and the like. For example, the kit for PCR can be used in a test tube or other suitable container, reaction buffer, deoxynucleotides (dNTPs), enzymes such as Taq polymerase reverse transcriptase, DNase, RNAse inhibitor, DEPC-water, sterilized water, and the like.

The kit may be applied to a sample collected from the oral cavity. Specifically, the kit can predict or diagnose the risk of a metabolic disease or a metabolic disease-related disease by a non-invasive method.

The kit may further include at least one collection device for sampling an oral cavity sample selected from the group consisting of an absorbent pad, a swab, a syringe, a spoon, a swab, and a toothpick for sampling the oral cavity of a subject, but is not limited thereto as long as it can collect the oral cavity sample.

The kit may additionally include an instructing description to collect the subject's sample in the mouth for the purpose of predicting or diagnosing the risk of a metabolic disease or metabolic disease-related disease.

As another example, in order to provide information required for predicting or diagnosing the risk of metabolic syndrome or metabolic syndrome-related diseases, the present invention provides a method of detecting at least a microorganism selected from the group consisting of *Neisseria* spp., *Granulicatella* spp. and *Peptococcus* spp.

As another example of the present invention, there is provided a method for detecting metabolic syndrome or metabolic syndrome-related diseases, which comprises the step of detecting at least one microorganism selected from the group consisting of a *Neisseria* spp., *Granulicatella* spp., and *Peptococcus* spp. and a method for providing information on the prediction or diagnosis of the risk of metabolic disease or metabolic disease-related disease.

The description for the composition of the prediction or diagnosis of the risk of metabolic syndrome or metabolic syndrome-related diseases can be applied to a method of detecting a microorganism, a method of the prediction or diagnosis of the risk of metabolic disease or metabolic disease-related disease, or a method for providing information on the prediction or diagnosis of the risk of metabolic disease or metabolic disease-related disease, etc.

Preferably, the method comprises the steps of: (a) collecting a test sample of a subject; (b) extracting genomic DNA from the test sample; (c) reacting the extracted genomic DNA with a primer specific to at least one microorganism selected from the group consisting of *Neisseria* spp., *Granulicatella* spp., and *Peptococcus* spp.; and (d) amplifying the reaction product.

In the above step (a), the term, "a test sample of a subject" refers to a sample taken from a person who is expected to have a metabolic disease or metabolic disease-related disease, for examples, tissue, cell, whole blood, serum, plasma saliva or urine, or preferably oral cavity of the person. The subject's oral cavity includes preferably oral epithelial cell, oral blood, oral saliva, oral calculus, oral plasma, and their solutions.

The conventional method for diagnosing metabolic syndrome have been problematic in that they cause additional stress due to invasive blood sampling and fasting blood glucose measurement. However, the present invention can be applied to the non-invasive method, particularly the oral cavity sampling method, thus reduces the stress of the subject.

The extraction of the genomic DNA from the test sample of the subject in the step (b) can be performed by applying a general technique known in the art. In step (c), a primer specific to at least one microorganism selected from the group consisting of *Neisseria* spp., *Granulicatella* spp., and *Peptococcus* spp. can be explained below.

The method of amplifying the reaction product in the step (d) may be carried out using conventional amplification techniques known in the art, for example, polymerase chain reaction (PCR), SYBR real time PCR, reverse transcription-polymerase chain reaction, multiplex PCR, touchdown PCR, PCR, nested PCR, booster PCR, real-time PCR, fractional display PCR, Rapid amplification of cDNA ends, Inverse PCR, VECTORET PCR, TAIL-PCR, Ligase chain reaction, Restriction chain reaction, Transcription-Selective replication of the target base sequence may be used, but the present invention is not limited thereto.

In the step (c), the step of comparing the amount of amplification product of the test sample with the amount of amplification product of the normal control sample can be further performed, and the subject can be determined to have the presence of occurrence or high risk of metabolic syndrome or metabolic syndrome-related diseases.

Preferably, when the amplification product of one or more microorganisms selected from the group consisting of *Neisseria* spp., and *Granulicatella* spp., is higher than that of the normal control sample, the occurrence or the risk of metabolic syndrome or metabolic syndrome-related diseases may be predicted or diagnosed.

In case that the step of amplifying the genomic DNA of at least one microorganism selected from the group consisting of *Neisseria* spp., for example *Neisseria elongata*, and *Granulicatella* spp., for example *Granulicatella adiacens* is performed by SYBR real time PCR, the occurrence or the risk of metabolic syndrome or metabolic syndrome-related diseases may be predicted or diagnosed for the subject, when P value (absolute quantitative value of the genomic DNA amplification product of *Neisseria* spp. and/or *Granulicatella* spp. in the detection sample)/(absolute quantitative value of the genomic DNA amplification product of the strain in the normal sample) with excluding the outlier (means±1.5*standard deviation) is 1.01 to 5.00, preferably 1.01 to 2.00 or 2.00 to 3.50. For example, when P value is 2.00 to 3.50, the risk of hypertension can be predicted or the occurrence of hypertension can be diagnosed.

$$P=\text{(absolute quantitative value of the genomic DNA amplification product of the strain in the detection sample)/(absolute quantitative value of the genomic DNA amplification product of the strain in the normal sample)} \quad \text{[Equation 1]}$$

When the calculated P value of *Neisseria* spp. is 1.1 or more, or preferably 1.1, and/or when the calculated P value of *Granulicatella* spp. is 1.4 or more, or preferably 1.4, the risk of metabolic syndrome or metabolic syndrome-related diseases can be predicted or diagnosed.

In addition, when the amount of the amplified product of the test sample for *Peptococcus* spp. is lower than that of the normal control sample, the risk of hypertension can be predicted or the occurrence of hypertension can be diagnosed.

In case that the step of amplifying the genomic DNA of *Peptococcus* spp. is performed by SYBR real time PCR, the occurrence or the risk of metabolic syndrome or metabolic syndrome-related diseases may be predicted or diagnosed for the subject, when P value (absolute quantitative value of the genomic DNA amplification product of *Peptococcus* spp. in the detection sample)/(absolute quantitative value of the genomic DNA amplification product of the strain in the normal sample) with excluding the outlier (means±1.5*standard deviation) is 0.01 to 0.99, preferably 0.05 to 0.90. For example, when P value is 0.05 to 0.90, the risk of hypertension can be predicted or the occurrence of hypertension can be diagnosed.

$$P=\text{(absolute quantitative value of the genomic DNA amplification product of the strain in the detection sample)/(absolute quantitative value of the genomic DNA amplification product of the strain in the normal sample)} \quad \text{[Equation 1]}$$

Preferably, the ratio of the amplification product of *Peptococcus* spp. and *Granulicatella* spp. in the test sample of the subject (the absolute quantitative value of amplification product of *Peptococcus* spp. strain in the sample: (the absolute quantitative value of the amplification product of *Granulicatella* spp. strain in the sample) is lower than that of the normal control sample, the risk of a metabolic disease or related disease-related syndrome can be predicted or diagnosed. In case that the step of amplifying the genomic DNA of *Peptococcus* spp. and *Granulicatella* spp. is performed by SYBR real time PCR, the occurrence or the risk of metabolic syndrome or metabolic syndrome-related diseases may be predicted or diagnosed for the subject, when each ratio of the amplification product of *Peptococcus* spp. and *Granulicatella* spp. ranges from the lower limit selected from the groups of 0.01, 0.03, 0.05 and 0.22 to the upper limit selected from the groups of 0.23, 0.6, 0.62, 1.4, and 1.5. In case that the genomic DNA sequencing is performed by high-throughput sequencing, the risk of metabolic syndrome or metabolic syndrome-related diseases can be predicted or diagnosed, when the quantificated value of genome frequency of *Peptococcus* spp. and *Granulicatella* spp. 0.0001 to 0.05.

In addition, since the present invention has first found that *Neisseria* spp., *Granulicatella* spp., and/or *Peptococcus* spp. are specifically increased or decreased in patients with metabolic syndrome or metabolic syndrome-related diseases, it can be used for the development of a new drug for treating metabolic syndrome or metabolic syndrome-related diseases, by using the relationship between the change in *Neisseria* spp., *Granulicatella* spp., and/or *Peptococcus* spp. microbiota and the disease state.

In a preferred embodiment, the present invention provides a method of screening a therapeutic agent or a prophylactic agent for a metabolic disease or a metabolic disease-related disease, comprising detecting change in at least one microbial community selected from the group consisting of *Neisseria* spp., *Granulicatella* spp., and *Peptococcus* spp., after treating with the candidate substance for prevention or treatment of metabolic syndrome.

Specifically, the present invention relates to a method for comparing change in at least one microbial community selected from the group consisting of *Neisseria* spp., *Granulicatella* spp., and *Peptococcus* spp., in the presence or absence of the candidate substance for prevention or treatment of metabolic syndrome, and the method can be applied to the method of screening a therapeutic agent or a prophylactic agent for a metabolic disease or a metabolic disease-related disease.

In other words, the degree of forming the microbial cluster for each *Neisseria* spp., *Granulicatella* spp., and *Peptococcus* spp. in a sample is measured and compared, in the presence or absence of the candidate substance for prevention or treatment of metabolic syndrome, and the candidate substance can be developed as a therapeutic agent or a prophylactic agent for a metabolic disease, when the degree of forming the microbial cluster is decreased in the presence of candidate substance.

The candidate substance includes various compounds with low molecular weight, compounds with high molecular weight, nucleic acid molecules (for example, DNA, RNA, PNA, etc.), proteins, sugars and lipids which can be a therapeutic agent or a prophylactic agent for metabolic syndrome or metabolic syndrome-related diseases But is not limited thereto.

Advantageous Effect

The composition of the present invention provides *Neisseria* spp., *Granulicatella* spp., and/or *Peptococcus* spp, as novel biomarkers for the prediction or the diagnosis of the risk of metabolic syndrome or metabolic syndrome-related diseases, and provides the method of the prediction or the diagnosis having an higher accuracy than the conventional method, and useful application due to non-invasively sampling and not requiring fasting conditions before sampling. It can also be used as a target for the development and control of new drugs for the prevention or treatment of metabolic syndrome or metabolic syndrome-related diseases.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

DESCRIPTION OF THE EMBODIMENTS

Hereinafter, the present invention will be described in detail with reference to examples. However, the following examples are illustrative of the present invention, and the present invention is not limited by the following examples.

Example 1. Study Subject and Sample Collection

This test was conducted on identical twins who participated in Korea's Healthy Twin Study. The twin identities were confirmed by the AmpFlSTR Indentifier Kit (15 autosomal short tandem repeat markers and one sex-determination marker) and a survey having 90% or higher of accuracy. The detailed methodology of the twin cohort was explained in previous articles (Sung, J., et al., Twin Research and Human Genetics, 2006.9 (6): 844-848).

The patients satisfying the criteria for metabolic syndrome and the healthy subjects were selected and their first molar plaque was collected. The plaque samples collected with a sterilized toothpick were stored in a saline solution containing 0.9% NaCl and stored frozen at −80° C. Metabolic syndrome patients were selected, if they met three or more of the following five criteria.

<Selection Criteria for Patient with Metabolic Syndrome>
1) Waist circumference: 90 cm or higher for male, and 85 cm or higher for female,
2) Blood triglyceride content: 150 mg/dL or higher,
3) Serum HDL cholesterol content: less than 40 mg/dL for men and less than 50 mg/dL for women;
4) Blood pressure: 130/85 mmHg or more; and
5) Fasting blood glucose: 100 mg/dL or higher.

Example 2. DNA Extraction of Oral Microorganisms

The frozen samples of Example 1 were transferred to a laboratory and genomic DNA was extracted by bead-beating extraction method. Toothpicks with tartar stones were homogenized with zirconia-silica beads and extracted with isopropanol precipitation.

Example 3 Sequencing of 16S rRNA of Oral Bacteria Using Next Generation Sequence Analysis The DNA extracted in Example 2 was subjected to PCR amplification using a 515F/806R primer targeting the V4 region of the bacteria (Macrogen, Ultra-high-throughput microbial community analysis on the Illumina HiSeq and MiSeq platforms). The primers include a forward primer consisting of SEQ ID NO: 4 and a reverse primer consisting of SEQ ID NO: 5 in Table 2.

TABLE 2

| Classification | SEQ ID NO | Nucleotide sequence |
|---|---|---|
| Forward primer | 4 | 5'-AATGATACGGCGACCACCGAGATCTACACTAT GGTAATTGTGTGCCAGCMGCCGCGGTAA-3' |
| Reverse primer | 5 | 5'-CAAGCAGAAGACGGCATACGAGATAGTCAGTC AGCCGGACTACHVGGGTWTCTAAT-3' |

The forward primer sequences includes adapter sequences (5'-AATGATACGGCGACCACCGAGATCTACAC-3'; SEQ ID NO.9), pad sequences (5'-TATGGTAATT-3'; SEQ ID NO.10), linker sequences (5'-GT-3"; SEQ ID NO.11), and conservative bacterial primers 515F (5'-GTGCCAGCMGCCGCGGTAA-3'; SEQ ID NO.12), where the reverse primer sequence comprises an adapter sequence (5'-CAAGCAGAAGACGGCATACGAGAT-3'; SEQ ID NO.13), 12-barcode sequence, 5'-AGTCAGTCAG-3'; SEQ ID NO.14), a linker sequence (5'-CC-3'; SEQ ID NO.15), and a preserved bacterial primer 806R (5'-GGAC-TACHVGGGTWTCTAAT-3'SEQ ID NO.16). The PCR mixture was composed of 10×reaction buffer, 2.5 mM dNTP, 12.5 pmole of primer, and 2.5 U of G-Taq polymerase (Cosmo, Seoul, Korea) Seconds, 50 to 60 seconds, and 72 to 90 seconds for 35 repetitions and a final extension phase of 72 to 10 minutes. The amplification product was sequenced using the MiSeq instrument from Illumina.

Example 4. Analysis of Oral Microbiota Using 16S rRNA

Figure 1:
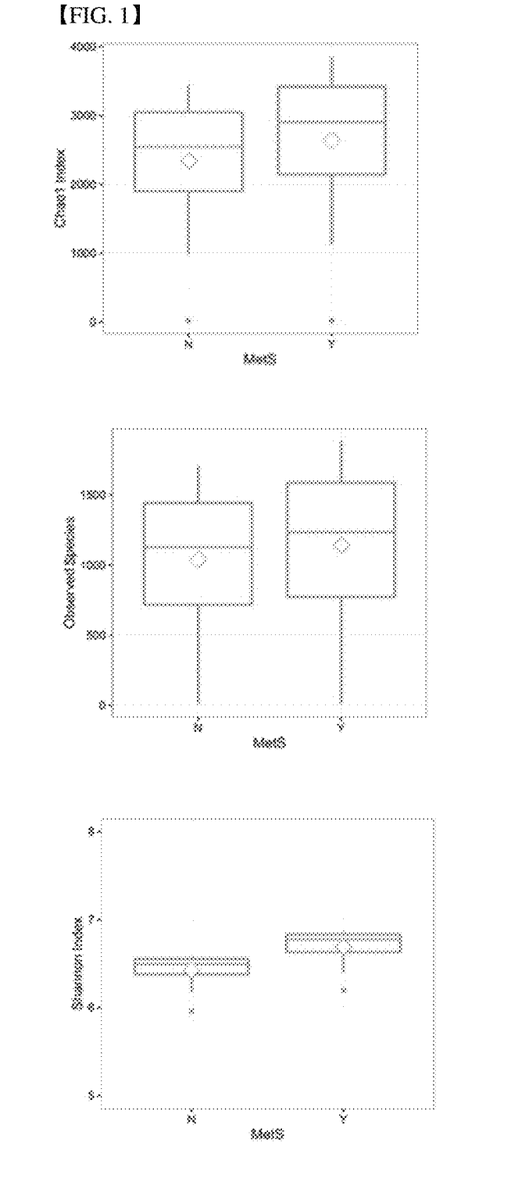
FIG. 1 shows the analysis results of oral microbial diversity for in the presence or absence of metabolic syndrome by Chao, observed species, and shannon index.
Figure 2:
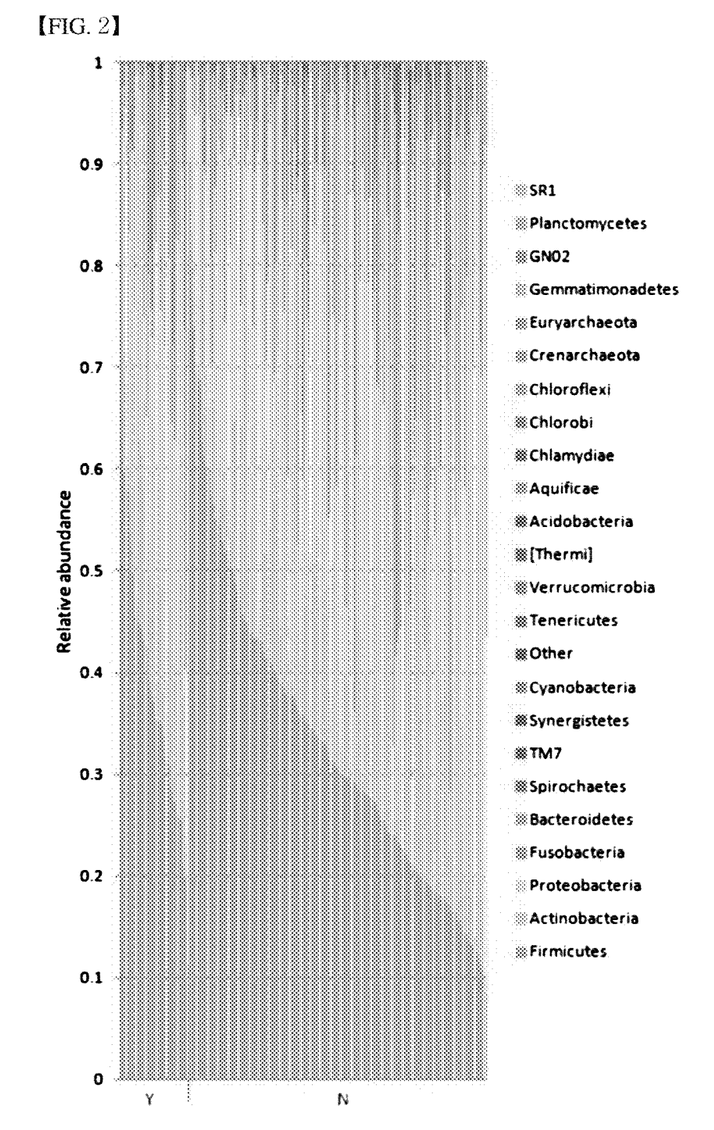
FIG. 2 shows the analysis result the oral microbiota structure in the presence or absence of metabolic syndrome.

The diversity and structure of oral bacterial community were analyzed using large-scale sequencing data generated by sequencing method with QIIME pipeline (Caporaso, J G, et al., QIIME allows analysis of high-throughput community sequencing data, Nat. 7 (5): 335-336). 228 oral samples in total of Korean twin cohort were collected and analyzed for bacterial 16S rRNA. The analysis result showed that the oral microbiota diversity of the metabolic syndrome group was significantly increased compared to the normal group (FIG. 1). As a result of analysis of the metabolic syndrome and normal control, three phyla at the phylum level constituted more than 70% of the microbiota population. Approximately 34% of Firmicutes, 32% of Proteobacteria and 17% of Actinobacteria were included and 38% of Firmicutes was increased and 32% of Proteobacteria was decreased in in the metabolic syndrome group (FIG. 2).

Example 5. Network Analysis of Oral Microbiota

Figure 3:
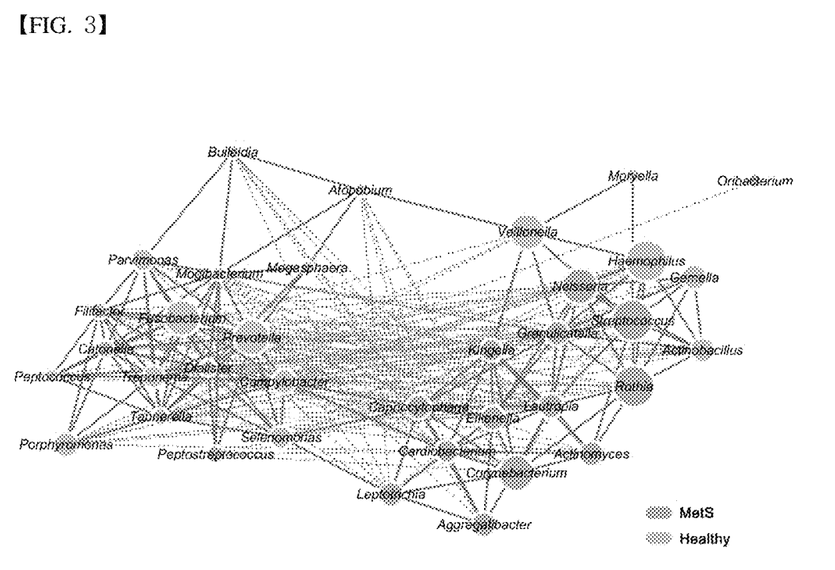
FIG. 3 is a result of analyzing the characteristic of oral microbiota through network analysis.

The network analysis was performed using Sparse Correlations for Compositional Data (SparCC) software to identify patterns of development of oral microbiota according to metabolic syndrome group and normal group. A network analysis of oral microbiota revealed that they formed a similar population of relatively large numbers of bacteria in the patient group of metabolic syndrome and the normal group (FIG. 3).

Figure 4:
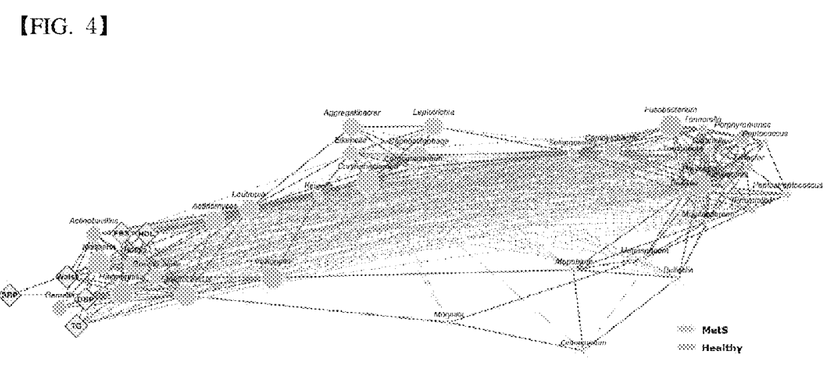
FIG. 4 is a graph showing the relationship between the oral microbiota and the metabolic syndrome through network analysis.

In addition, the network analysis of oral microbiota and the variables associated with metabolic syndrome revealed that *Streptococcus* spp., *Granulicatella* spp., *Neisseria* spp., *Hemophilus* spp., *Actinobacillus* spp., and *Rossia* spp. formed a significant network (FIG. 4).

Figure 5:
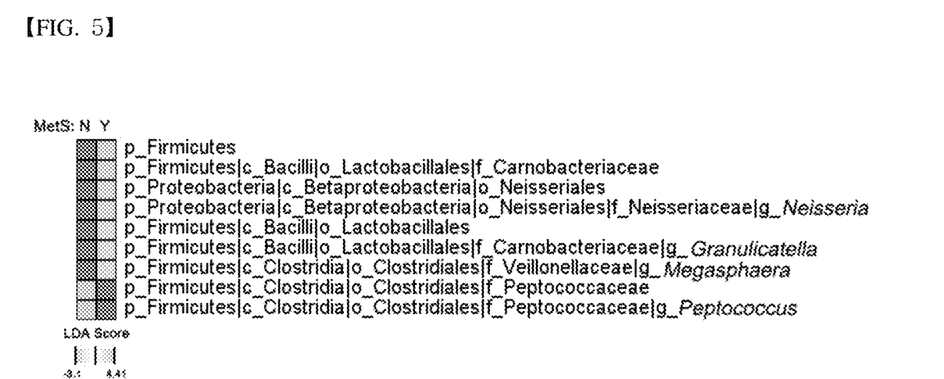
FIG. 5 shows the results of oral bacteria increased in the metabolic syndrome group and the normal control group using the univariate analysis tool of LEfSE software.

Example 6. Analysis of Oral Bacterial Biomarkers for Diagnosis of Metabolic Syndrome Univariate analysis was performed using LEfSe to identify the oral bacterial biomarkers for the diagnosis of metabolic syndrome. LEfSe is an analytical tool that validates the initial analysis results through the post-Wilcoxon rank-sum analysis after identification of microbial biomarkers through Kruskal-Willis analysis. Biomarkers were analyzed and the influence of biomarkers was assessed by the Linear Discriminant Analysis (LDA) analysis of LEfSe software (Segata, N., et al., Genome Biol., 2011. 12 (6): p. The analysis results of oral bacterial biomarker performed by univariate analysis showed that *Neisseria* spp. (LDA score: 4.05) and *Granulicatella* spp. (LDA score: 3.49) (FIG. 5) had more significant effect on the patient group, and *Peptococcus* spp. (LDA score: 3.1) had more significant effect on the normal group (FIG. 5).

Figure 6:
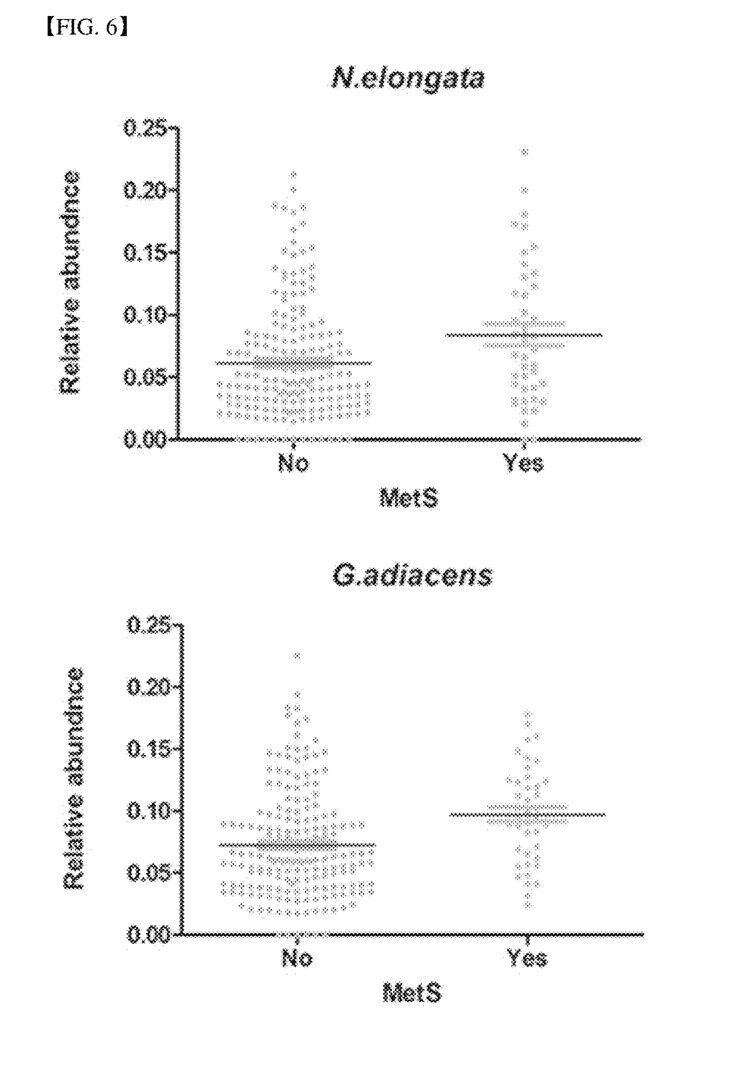
FIG. 6 shows the relationship between the metabolic syndrome and specific oral bacteria using MaAsLin of a multivariate analysis tool that corrects twin relationship, sex, and age.

Example 7. Correlation Analysis Between Oral Microbiota and Metabolic Syndrome Using MaAsLin software, which can control confounding variables, we have identified oral bacteria that can identify metabolic syndrome through multivariate analysis. Multivariate analysis was performed by controlling the age and gender of the subjects after assigning metabolic syndrome as an independent variable and oral microbiota as a dependent variable. As a result of multivariate analysis using the age and gender of the subjects as a correction factor, *Neisseria elongata* (r coefficient=0.024, q value (p value corrected for false positive)=0.136) of *Neisseria* spp., and *Granulicatella adiacens* (r coefficient=0.019, q value (p value corrected for false positives)=0.222) of *Granulicatella* spp. were analyzed to have a significant correlation with the metabolic syndrome (FIG. 6).

Example 8. Detection of Metabolic Syndrome Using Absolute Quantitative Analysis SYBR real-time PCR, one of the quantitative PCR methods, was used to confirm the possibility of detection for metabolic syndrome by detection of three types of oral microbiota, which were analyzed as having a significant correlation in Metabolic Syndrome in Examples 6 and 7. The absolute amount of *Neisseria* spp., *Granulicatella* spp., and *Peptococcus* spp., which the subjects actually possess, were measured.

In order to make a standard curve for absolute quantification, the genomic DNA was extracted from the culture of the type strains of *Neisseria* spp., *Granulicatella* spp., and *Peptococcus* spp., and amplified by PCR, and the cloned products were made and used by dilution with 10 times serial Dilution method. Real-time PCR was performed for the bacterial DNA extracted in Example 2, with the standard curve. The real-time PCR mixture consisted of 50 pmole of SYBR master mix (Applied Biosystems, Foster City, Calif.) with a total of 25 μl. The PCR reaction was denaturation at 95 for 15 min, 95 to 30 sec, and 40 repetitions per second.

Figure 7:
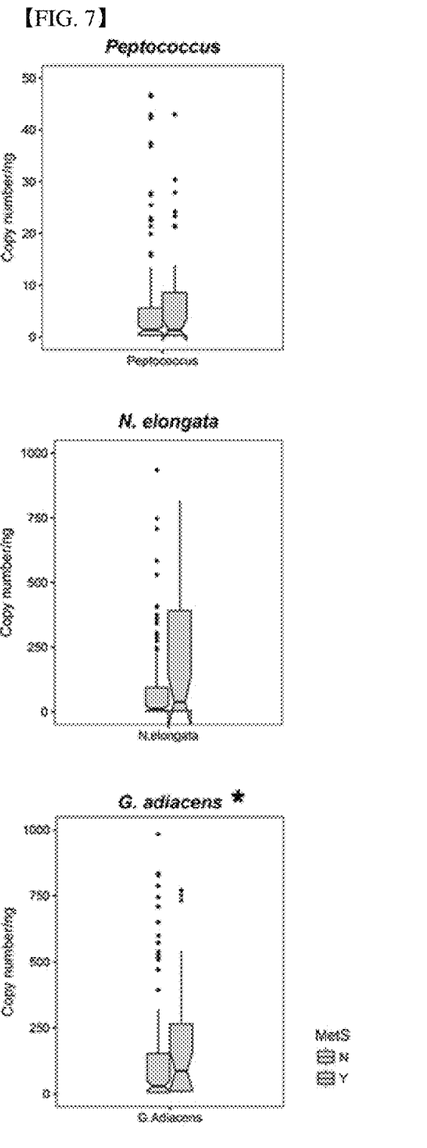
FIG. 7 shows the result of quantitative analysis of *Neisseria elongata*, *Granulicatella adiacens*, and *Peptococcus* using SYBR real-time PCR of an absolute quantitative analysis method.
Figure 8:
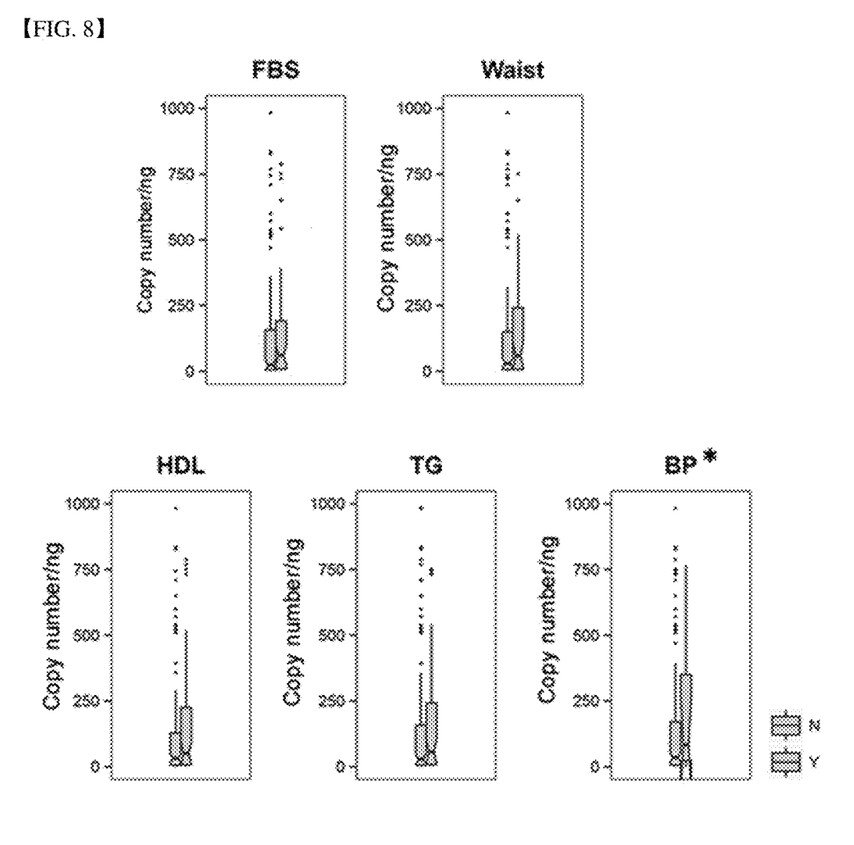
FIG. 8 is the result of the absolute amount change of *Granulicatella* spp. according to each clinical indicator which can define the metabolic syndrome.

The absolute quantification results are shown in FIG. 7 and FIG. 8. *Granulicatella* spp., showed an average of 2514 copy number/ng (DNA) in the metabolic syndrome group and 2358 copy number/ng (DNA) in the normal control group were amplified (P=1.07 calculated by Equation 1), and 4963 copy number/ng (DNA) in the high blood pressure group and 1675 copy number/ng (DNA) in the low blood pressure group among the clinical criteria for the diagnosis of the metabolic syndrome was amplified (P=2.96 calculated by Equation 1), resulting in being significantly related to blood pressure. Thus, it has been confirmed that bacterial strains can be detected by using primers for detecting oral bacterial strains and PCR, and thus, can be used for predicting or diagnosing the risk of metabolic syndrome.

$P$=(absolute quantitative value of the genomic DNA amplification product of the strain in the detection sample)/(absolute quantitative value of the genomic DNA amplification product of the strain in the normal sample) [Equation 1]

By using the number of genome copies of bacteria estimated by real-time PCR analysis, the ratio of *Granulicatella* spp. and *Peptococcus* spp. in the normal and metabolic syndrome groups were calculated. The ratio was calculated by dividing the number of genome copies of *Peptococcus* spp. by the number of genome copies of *Granulicatella* spp. The same analysis was also performed based on the relative frequency of oral bacteria estimated by large-scale sequencing method.

Figure 9:
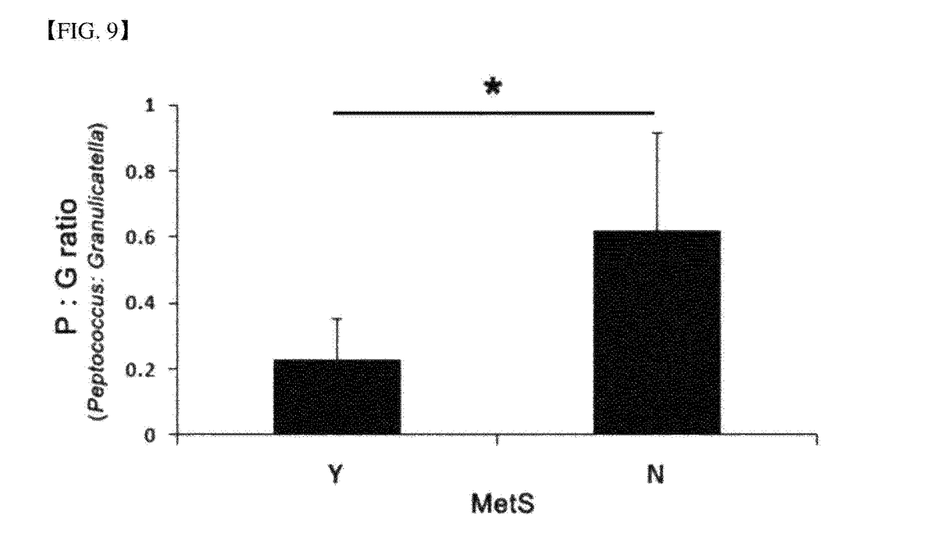
FIG. 9 shows the result of measuring the ratio of the absolute quantitative analysis for *Peptococcus* spp. and *Granulicatella* spp.
Figure 10:
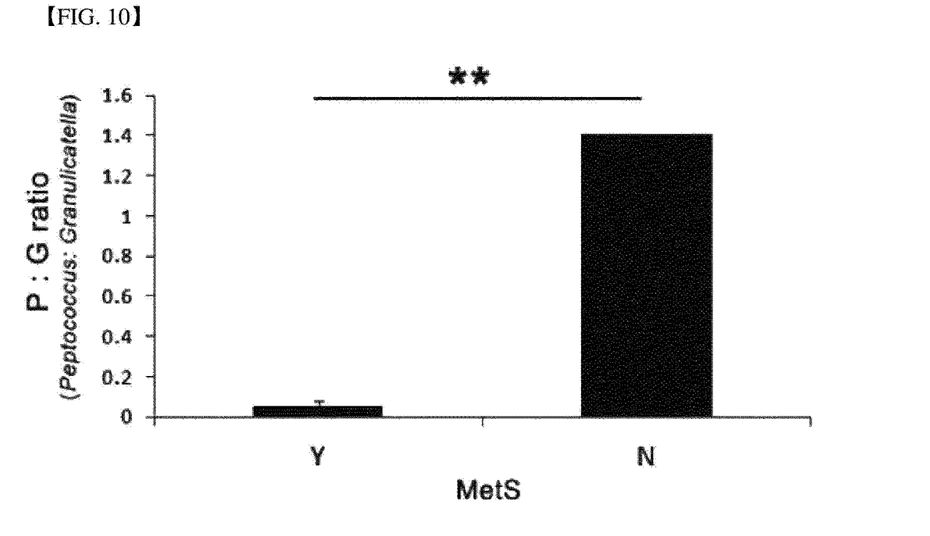
FIG. 10 shows the result of measuring the ratio of the relative quantitative analysis for *Peptococcus* spp. and *Granulicatella* spp. obtained by oral microbiome analysis.

The ratio of *Peptococcus* spp. to *Granulicatella* spp. in the normal group and the metabolic syndrome group is shown in FIG. 9, and the ratio is 0.62 in the normal group and 0.22 in the patient group. When the same analytical method was applied to the relative frequency of oral bacteria estimated from the oral microbiota analysis, the ratio of *Peptococcus* spp. to *Granulicatella* spp. was 1.4 in the normal group and 0.05 in the patient group (FIG. 10).

The invention claimed is:

1. A method of diagnosis of risk of metabolic syndrome or metabolic syndrome-related diseases, comprising
amplifying genomic DNA of microorganisms comprising *Peptococcus* spp. and *Granulicatella* spp. from an oral sample of a subject using a primer pairs of SEQ ID NOs: 1 and 2 and a primer pair of SEQ ID NOs: 3 and 4,
obtaining a ratio of an amplification product amount of *Peptococcus* spp. and *Granulicatella* spp., wherein the amplification product amount is an absolute quantitative value obtained by performing absolute quantitative analysis or a relative quantitative value obtained by performing relative quantitative analysis,
comparing the ratio of the amplification product amount of *Peptococcus* spp. and *Granulicatella* spp. with that of a normal control sample,
determining the subject has occurrence or risk of metabolic syndrome or metabolic syndrome-related diseases, when
(a) the ratio of the amplification product amount of *Peptococcus* spp. and *Granulicatella* spp. of the subject is lower than that of the normal control sample, and
(b) the ratio of the absolute quantitative value of *Peptococcus* spp. and *Granulicatella* spp. is 0.01 to 0.6 or the ratio of the relative quantitative value of *Peptococcus* spp. and *Granulicatella* spp. is 0.0001 to 0.05, and
treating the subject determined to have occurrence or risk of metabolic syndrome or metabolic syndrome-related diseases,
wherein the metabolic syndrome-related disease is at least one selected from the group consisting of obesity, hypertension, diabetes, insulin resistance syndrome, hyperlipidemia, cardiovascular disease, inflammatory bowel disease, atopic disease and allergic disease.

2. The method according to claim 1, wherein the step of amplifying genomic DNA of microorganisms comprises:
reacting genomic DNA of microorganisms comprising *Peptococcus* spp. and *Granulicatella* spp. obtained from the oral sample of a subject with the primer pairs; and
amplifying the reaction product.

3. The method according to claim 2, wherein the microorganisms further comprises *Neisseria* spp.

4. The method according to claim 2, wherein said sample is at least one selected from the group consisting of oral epithelial cells, oral blood, oral saliva, oral calculus, oral plasma, and their solution.

5. The method according to claim 1, wherein the step of amplifying is performed by real time PCR.

6. The method according to claim 1, wherein the step of amplifying is performed by high-throughput sequencing.

* * * * *